US010525191B1

(12) United States Patent
Ackerman (10) Patent No.: US 10,525,191 B1
(45) Date of Patent: Jan. 7, 2020

(54) EAR CANAL IRRIGATION SYSTEM AND METHOD

(71) Applicant: Christopher Ackerman, Keyport, NJ (US)

(72) Inventor: Christopher Ackerman, Keyport, NJ (US)

( * ) Notice: Subject to any disclaimer, the term of this patent is extended or adjusted under 35 U.S.C. 154(b) by 0 days.

(21) Appl. No.: 16/438,635

(22) Filed: Jun. 12, 2019

(51) Int. Cl.
*A61M 3/00* (2006.01)
*A61M 39/10* (2006.01)
*A61M 39/12* (2006.01)
*A61F 11/00* (2006.01)
*A61M 3/02* (2006.01)
*A61B 90/00* (2016.01)

(52) U.S. Cl.
CPC .......... *A61M 3/0279* (2013.01); *A61B 90/05* (2016.02); *A61F 11/006* (2013.01); *A61M 3/0262* (2013.01); *A61M 2210/0662* (2013.01)

(58) Field of Classification Search
CPC ......... A61B 90/00; A61B 90/05; A61F 11/00; A61F 11/006; A61M 2210/0662; A61M 3/02; A61M 3/0262; A61M 3/0279; B65D 83/30; B65D 83/303; B65D 25/38; B65D 25/385; B65D 25/40; B65D 25/42; B65D 25/44; B65D 25/46; B65D 25/465; B65D 25/48
See application file for complete search history.

(56) References Cited

U.S. PATENT DOCUMENTS

| | | | | | |
|---|---|---|---|---|---|
| 989,839 | A | * | 4/1911 | Fowler | A61M 3/0279 604/276 |
| 3,107,671 | A | * | 10/1963 | Farina | A61M 3/0279 604/118 |
| 3,648,696 | A | * | 3/1972 | Keith | A61D 1/02 604/310 |
| 4,559,940 | A | * | 12/1985 | McGinnis | A61M 16/0488 128/202.28 |
| 5,114,415 | A | * | 5/1992 | Shedlock | A61M 1/008 604/319 |
| 5,527,275 | A | * | 6/1996 | Ginsberg | A61M 3/02 604/38 |
| 5,833,675 | A | * | 11/1998 | Garcia | A61M 3/0262 604/310 |
| 5,944,711 | A | * | 8/1999 | Pender | A61B 1/227 604/514 |
| 5,988,530 | A | * | 11/1999 | Rockefeller | B05B 15/30 239/333 |
| 6,238,377 | B1 | * | 5/2001 | Liu | A61H 35/04 604/289 |

(Continued)

*Primary Examiner* — Adam Marcetich
(74) *Attorney, Agent, or Firm* — Christopher Mayle; John D. Houvener; Bold IP, PLLC (57) ABSTRACT

An ear canal irrigator system having a hand-held spray bottle and a conduit tube connected to the spray bottle by a series of components that allow the tube to be connected without being screwed on and also prevents leakage of fluid. The system further includes an insertion tube connected to the conduit tube by a connecting piece having a splash guard, whereby the insertion tube is configured to be placed at or near the ear canal of a user. The insertion tube is shorter in length that the conduit tube and has a smaller diameter than the conduit tube so that when the fluid flows through the connecting piece into the insertion tube, the fluid has a more powerful fluid stream.

19 Claims, 5 Drawing Sheets

(56) References Cited

U.S. PATENT DOCUMENTS

| | | | |
|---|---|---|---|
| 8,747,372 B1* | 6/2014 | Schultz | A61M 3/0262 |
| | | | 604/289 |
| 9,314,804 B1* | 4/2016 | Harrower | B05B 1/28 |
| 2002/0022796 A1* | 2/2002 | Lawrence | A61M 1/0084 |
| | | | 604/27 |
| 2003/0229322 A1* | 12/2003 | Macrae | A61F 11/002 |
| | | | 604/275 |
| 2010/0114016 A1* | 5/2010 | Gallo | A61H 35/04 |
| | | | 604/73 |
| 2011/0139831 A1* | 6/2011 | Rowland | B08B 5/02 |
| | | | 239/104 |
| 2014/0083535 A1* | 3/2014 | Van Ryswyk | F17D 1/14 |
| | | | 137/565.01 |

* cited by examiner

EAR CANAL IRRIGATION SYSTEM AND METHOD

FIELD OF THE DISCLOSURE

The field of disclosure relates generally to ear irrigation devices. More particularly, the field of disclosure relates generally to ear irrigation devices for irrigation of an ear canal allowing for more water pressure while protecting the user and environment from the splash back.

BACKGROUND

Ears naturally secrete cerumen or wax ("earwax") to protect and lubricate the ears. The earwax acts as a self-cleaning agent produced by your body. Wax keeps out debris out and hinders bacterial growth. Wax works its way out of the ears naturally through chewing and other jaw motions. Normally, the human body keeps a certain amount of earwax in the ears but when there is too much earwax present, a blockage in the ear may occur. This may result in damage to the ear canal and ear drum of the ear over time causing earaches, ringing in the ears, or temporary hearing loss.

Currently, there are a few methods utilized to prevent the buildup of excess wax. The safest way to remove wax buildup from your ears is to visit a doctor but this may not be practical for everyone because of time and money concerns. Some people use devices such as cotton swabs or Q-Tips® to remove excess wax and debris from their ear. However, cotton swabs may damage the ear canal and ear drum, and even push wax further down into the ear. Others use syringes wherein a large syringe is used to pump water into the ear. Syringing is a dangerous procedure because it is difficult to control water pressure, which may cause damage to the ear and can result in an infection, perforation of the eardrum, and trauma to the ear canal.

Removing excess wax with ear irrigation is one of the safer ways way to minimize the risk of damage to the ear. Irrigation involves using the controlled, pressurized flow of water so that the ear wax is softened, broken up, and then washed out of the ear, preventing the build-up of ear wax.

Previous irrigator devices do not have an effective way to increase water pressure or a way to prevent splash back and the prevention of leakage. Thus, there exists a need for an improved irrigation device that allows for smooth transition for water out and into the ear canal with additional targeted water pressure.

SUMMARY

Embodiments of the present disclosure are described in detail below with reference to the following drawings. These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure.

In one aspect, embodiments in the present description are directed to an ear canal irrigation system, the ear canal irrigation system comprising, a spray bottle, the spray bottle comprising a nozzle, a head, and a reservoir, the reservoir having a spray tube extending therethrough, wherein the reservoir is configured to contain a fluid, a conduit tube, a connector; and an insertion tube, wherein the conduit tube is configured to connect to the connector at one end of the connector, and wherein the insertion tube is configured to connect to the connector at a second end of the connector, and further wherein the conduit tube and the insertion tube each have an aperture extending therethrough, wherein the aperture of the insertion tube is of a smaller diameter than the aperture of the conduit tube, wherein the connector allows a transition of the fluid from the conduit tube to the insertion tube while reducing the overall diameter of the fluid.

In one aspect, embodiments in the present description are directed to a method of using an ear canal irrigation device, the method comprising connecting a nozzle attachment to a nozzle of a spray bottle, connecting a conduit tube to the nozzle attachment, connecting the conduit tube to a first end of a connector, wherein the connector further comprises a splash guard, connecting an insertion tube to a second end of the connector, wherein the conduit tube and the insertion tube have an aperture therethrough, wherein the aperture of the insertion tube is of a smaller diameter than the conduit tube, and wherein the connector allows for a transition of a fluid from the conduit tube to the insertion tube while reducing the overall diameter of the fluid; and orienting the insertion tube at or near the ear canal of a user.

In one aspect, embodiments in the present description are directed to an ear canal irrigation system, the ear canal irrigation system comprising, a spray bottle, the spray bottle comprising a nozzle, a head, and a reservoir, the reservoir having a spray tube extending therethrough, wherein the reservoir is configured to contain a fluid, a nozzle attachment, wherein the nozzle attachment is configured to connect to the nozzle, a conduit tube, wherein the conduit tube is configured to connect to the nozzle attachment, a connector; an insertion tube, wherein the conduit tube is configured to connect to the connector at one end of the connector, and wherein the insertion tube is configured to connect to the connector at a second end of the connector, and further wherein the conduit tube and the insertion tube each have an aperture extending therethrough, wherein the aperture of the insertion tube is of a smaller diameter than the aperture of the conduit tube, wherein the connector allows a transition of the fluid from the conduit tube to the insertion tube while reducing the overall diameter of the fluid, and a cover piece, wherein the nozzle attachment is configured to connect to a cover piece, the cover piece configured so that when connected to the nozzle attachment, the cover piece acts as a reinforcing seal to prevent any leakage of fluid as the fluid exits the nozzle into the conduit tube.

BRIEF DESCRIPTION OF THE DRAWINGS

Embodiments of the present disclosure are described in detail below with reference to the following drawings. These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure.

DETAILED DESCRIPTION

In the Summary above and in this Detailed Description, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises", and grammatical equivalents thereof are used herein to mean that other components, ingredients, steps, among others, are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)–(a second number)," this means a range whose limit is the second number. For example, 25 to 100 mm means a range whose lower limit is 25 mm and upper limit is 100 mm.

Certain terminology and derivations thereof may be used in the following description for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The present disclosure recognizes the unsolved need for an improved system and method for an ear canal irrigation device that provides a more effective way to increase water pressure and control for delivering bursts of pressurized water while incorporating a splash guard using a custom plastic mold that is configured to connect a larger conduit tube to a smaller insertion tube. The new plastic mold creates a smooth transition for funneling fluid out and into the ear canal. By reducing the total diameter of the fluid stream, additional pressure is created. The custom plastic mold also serves as a built in splash guard, which is an additional advantage offered by embodiments described herein.

Figure 1:
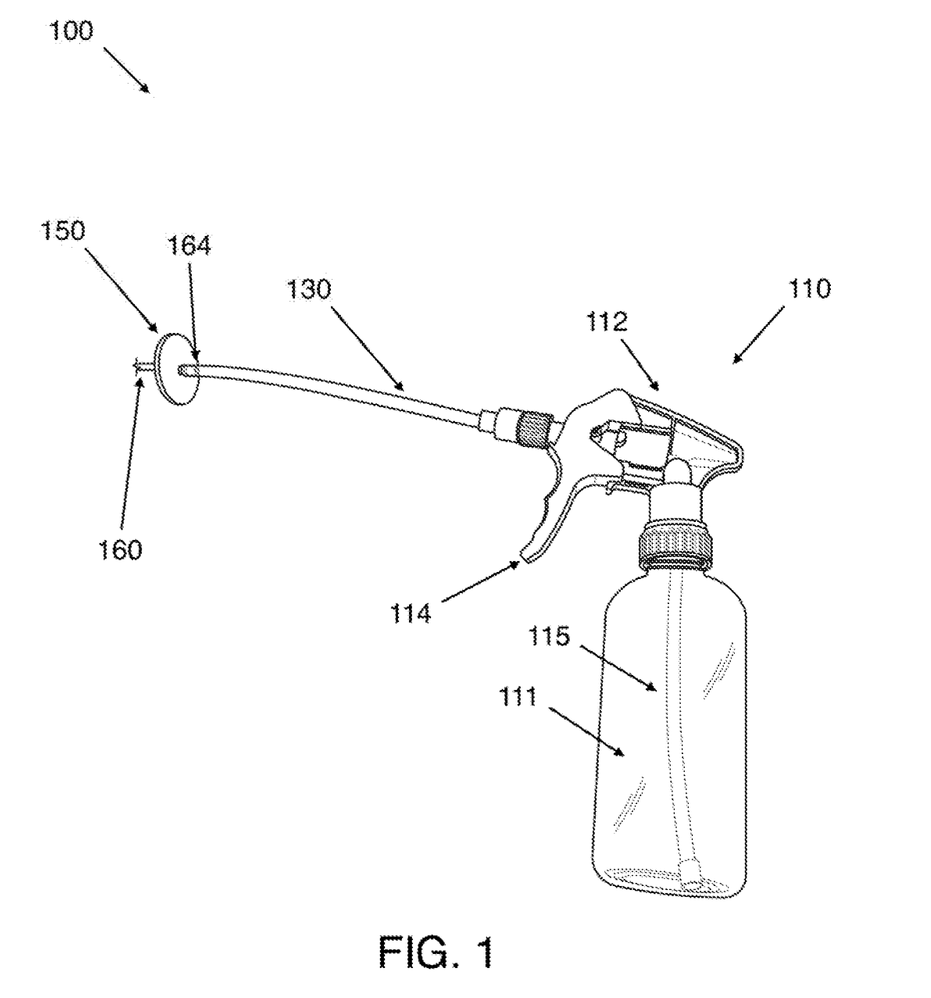
FIG. 1 illustrates a perspective view of an ear canal irrigation system according to an illustrative embodiment.
Figure 2:
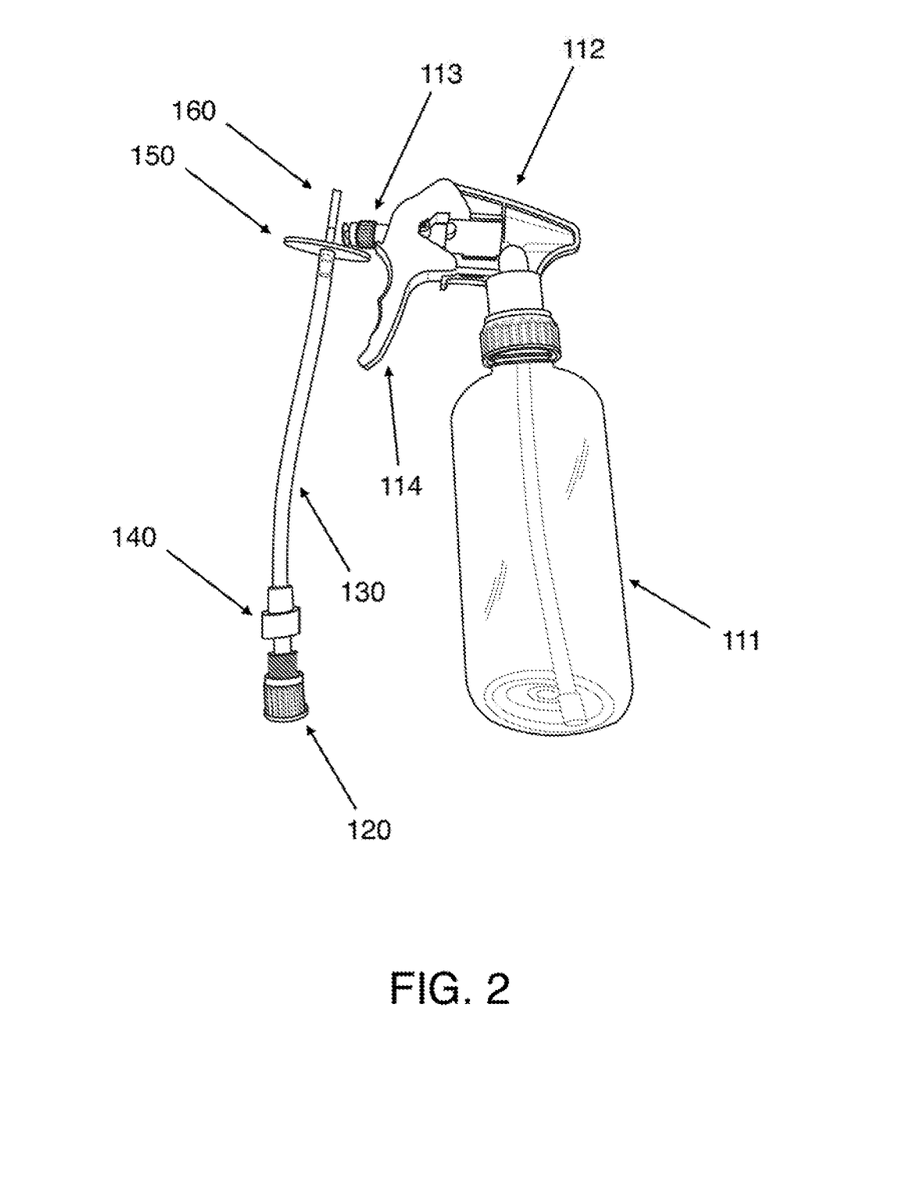
FIG. 2 illustrates a perspective view of an ear canal irrigation system with the nozzle attachment separated from the nozzle of the spray bottle.

Turning to FIGS. 1 and 2, FIG. 1 depicts an embodiment of the present invention for ear canal irrigation system 100 and FIG. 2 depicts a perspective view of an ear canal irrigation system with the nozzle attachment separated from the nozzle of the spray bottle. Numbers referenced below may be found in both FIG. 1 and FIG. 2. Ear canal irrigation system 100 may include a spray bottle such as spray bottle 110. Spray bottle 110, in one exemplary embodiment, includes a reservoir such as reservoir 111 for holding a fluid. In one embodiment, the fluid that may be contained within reservoir 111 may be water. In another embodiment, the fluid may be a saline solution or any other type of fluid as desired by the user.

Spray bottle 110 may also include a head such as head 112 and a nozzle, such as nozzle 113, as shown in FIG. 2. To further elaborate, head 112 may include, in some embodiments, an internal chamber and a pump. Nozzle 113 may further be configured to be an outlet for the fluid. Nozzle 113 may be connected to a nozzle attachment such as nozzle attachment 120 (as shown in FIG. 2), and a trigger mechanism such as trigger mechanism 114 (as shown in FIG. 1). In one embodiment, when trigger mechanism 114 is depressed, a pump (not shown) positioned inside of head 112 may be activated to force fluid from reservoir 111 into a spray bottle tube, such as spray bottle tube 115, then into an internal chamber (not shown) of head 112, and then out through nozzle 113. Pump may be an automatic or mechanical pump, such as a compressor, or a manual pump.

Spray bottle 110 may be made of a thermoplastic polymer, such as but not limited to polycarbonate, polyethylene terephthalate, polybutylene terephthalate, polyurethane or other moldable plastics. Other types of materials may also be used to form spray bottle 110 (and the various components of ear canal irrigations system 100) including glass, metal, or a combination thereof. The size and shape of reservoir 111 of spray bottle 110 and the other components of spray bottle 110 are for illustration purposes and may be of various shapes and sizes. For example, reservoir 111 may be cylindrical, spherical, octagonal rectangular, or any other three-dimensional shape. Reservoir 111 may have a bottom with concave edges and a dome shaped bottom in one exemplary embodiment. In one non-limiting embodiment, reservoir 111 may have one or more screw threads for attachment to head 112 wherein reservoir 111 incorporates female screw threads and head 112 incorporates male screw threads for attachment. Head 112 may be connected to a spray bottle tube, such as spray bottle tube 115, having a first open end and a second open end, wherein spray bottle tube 115 extends substantially into reservoir 111, and wherein the second end of the first tube is positioned near or at the inside bottom level of reservoir 111.

Figure 3:
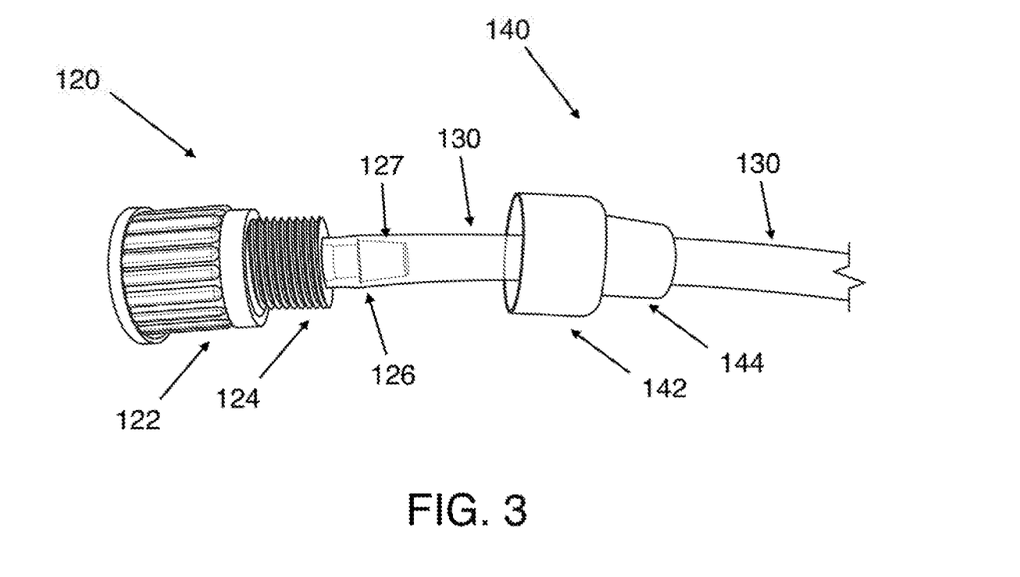
FIG. 3 illustrates a perspective view of the nozzle attachment and cover piece with the conduit tube attached.

FIG. 2 includes a nozzle attachment, shown as nozzle attachment 120, which is configured to attach or connect to nozzle 113. In FIG. 1 nozzle attachment 120 is connected to nozzle 113, but in FIG. 2 nozzle attachment 120, as well as conduit tube 130 and connector 150 are disconnected from nozzle 113. As illustrated in FIG. 3, nozzle attachment 120 may have a bottom component such as bottom component 122, a middle component such as middle component 124, and a top component such as top component 126. It is noted that nozzle attachment 120 may have many different shapes and sizes other than that shown in FIG. 2.

Nozzle attachment 120, in one embodiment, is designed to screw onto or otherwise fasten to nozzle 113 with the intention of connecting to a conduit tube such as conduit tube 130. Once nozzle attachment 120 is screwed on, nozzle attachment 120 is configured so that conduit tube 130 may connect to spray bottle 110 via nozzle attachment 120 without the need to screw or fasten while forming an air tight seal allowing fluid to flow freely out of spray bottle 110 through conduit tube 130. This is an advantage over existing prior art because it allows conduit tube 130 to positioned and repositioned in a more efficient manner and the components of the system may easily be removed and replaced. It is desirable that the threading attachment may be particularly advantageous to form a tight seal (ex. air tight seal) that may prevent the excessive leaking of any fluid flowing from reservoir 111 through internal head 112 and nozzle attachment 113 to conduit tube 130.

Bottom component 122, middle component 124, and top component 126 of nozzle attachment 120 may have apertures therethrough whereby the apertures in bottom component 122, middle component 124, and top component 126 of the nozzle attachment 120 may be in axial alignment. In one embodiment, bottom component 122 and middle component 124 may be generally cylindrical in shape, however, any other shapes may be used as well. In one embodiment, the aperture of middle component 124 may have a diameter less than the diameter of the aperture of bottom component 122. In one exemplary embodiment, bottom component 122 may have one or more internal screw threads for attachment to nozzle 113 (as shown in FIGS. 1 and 2). In one, non-limiting embodiment, nozzle attachment 120 may incorporate female screw threads positioned internally within bottom component 122 of nozzle attachment 120 and nozzle 113 may have complementary male screw threads for attachment to each other. Those of ordinary skill in the art may appreciate that this configuration may be reversed, such that the nozzle attachment 120 may incorporate the make screw threads and the nozzle 113 may incorporate the female screw threads in alternative embodiments. In other embodiments, other attachment mechanisms may also be used, including using fasteners, adhesives, or a combination of attachment mechanisms.

Top component 126 may comprise a bottom in the form of a shaft and top end having conical shape component such as conical shape component 127 with a vertex angle and inclination wherein conduit tube 130 may be connected and secured by the outward force of the conical shape component 127 against conduit tube 130 when the inner surface of conduit tube 130 is slid or positioned over conical shape component 127. In one or more non-limiting embodiments, conduit tube 130 may be made of plastic or any other material that is fluid-impermeable material, light weight, and transparent. Conduit tube 130 is preferably flexible, but may also be semi-rigid or rigid in some embodiments. Conduit tube 130 may be slid over conical shape component 127 until the first end of conduit tube 130 reaches the top surface of middle component 124 of nozzle attachment 120.

Figure 4:
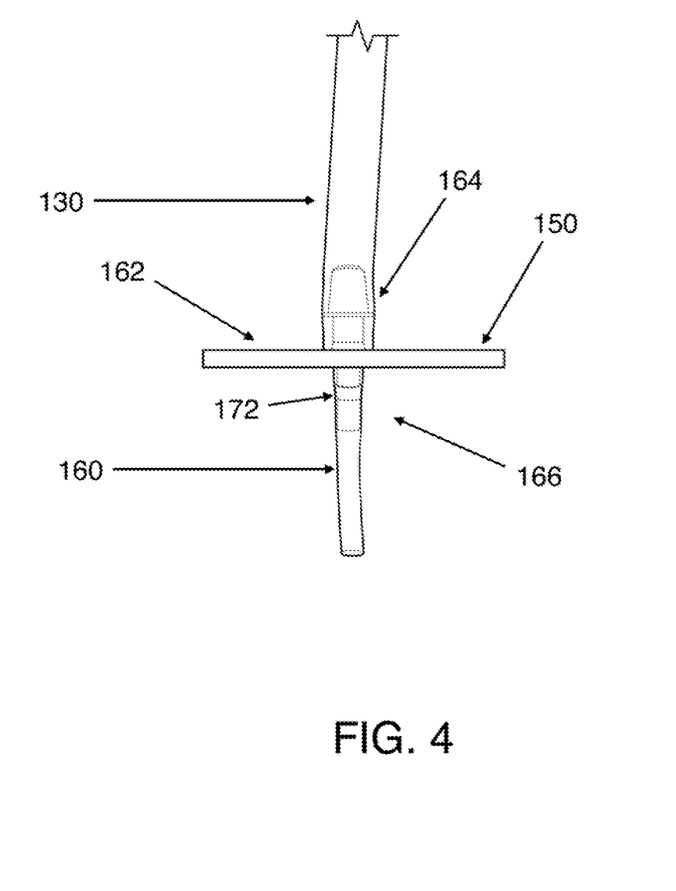
FIG. 4 illustrates a side view of an exemplary connector with a conduit tube and an insertion tube attached.

As illustrated in FIG. 3 and FIG. 4, nozzle attachment 120 may be connected to a cover piece such as cover piece 140. Cover piece 140 may function so that when screwed onto nozzle attachment 120, cover piece 140 acts as a reinforcing seal and prevents any leakage of fluid as the fluid exits nozzle 113 and enters conduit tube 130. Cover piece 140 may have a bottom component such as bottom component 142 and a top component such as top component 144. Bottom component 142 and top component 144 may have apertures therethrough whereby the apertures in bottom component 142 and top component 144 may be in axial alignment. The aperture of top component 144 may have a diameter less than the diameter of the aperture of bottom component 142.

In one embodiment, cover piece 14 may be configured to screw onto nozzle attachment 120. In one example arrangement, middle component 124 of nozzle attachment 120 may have one or more screw threads for attachment to cover piece 140 whereby nozzle attachment 120 incorporates male screw threads positioned on middle component 124 of nozzle attachment 120 and bottom component 142 of cover piece 140 has female screw threads for attachment. However, this thread configuration may be reversed in alternative embodiments. Top component 144 and bottom component 142 of cover piece 140 may be cylindrical in shape with circular openings allowing cover piece 140 to slide over conduit tube 130 until bottom component 144 of cover piece 140 comes in contact with middle component 124 of nozzle attachment 120 (as shown in FIG. 3). Top component 144 of cover piece 140 may be manufactured to a dimension to allow it to form a waterproof seal when conduit tube 130 is attached to top component 122 of nozzle attachment 120 and cover piece 140 is secured in place over nozzle attachment 120. In a further non-limiting embodiment, nozzle 113, nozzle attachment 120, cover piece 140, and conduit tube 130, or any combination may be permanently attached rather than being each separately removeably attached to each other.

Turning to FIG. 4, FIG. 4 illustrates a side view of an exemplary connector with a conduit tube (e.g. conduit tube 130) and an insertion tube (e.g. insertion tube 160) attached. As illustrated in FIG. 4, the second end of conduit tube 130 may be connected to a connector such as connector 150 (also shown in FIG. 1). Connector 150 may be configured to connect conduit tube 130 to a smaller insertion tube such as insertion tube 160. In one embodiment, insertion tube 160 may be placeable or insertable into an ear or ear canal of a user in order for the fluid flowing from spray bottle 110 to enter the ear or ear canal of the user. Insertion tube 160 is configured to have a small diameter in order to prevent the flushing fluid from exiting the ear canal. Insertion tube 160 may be described as having a narrow passageway. In one or more non-limiting embodiments, insertion tube 160 may be made of plastic or any other material that is fluid-impermeable material, light weight, flexible, and transparent. Insertion tube 160 may also be semi-rigid or rigid in some non-limiting embodiments.

In one embodiment, connector 150, as shown in FIG. 4, is configured to create a smooth transition of fluid flow from the larger conduit tube 130 to the smaller insertion tube 160. FIG. 4 illustrate that conduit tube 130 may be configured to have a larger diameter than the diameter of insertion tube 160. Connector 150 also reduces the overall diameter of the fluid stream as the fluid passes from conduit tube 130 through connector 150 and into insertion tube 160. The overall design and connection between conduit tube 130, connector 150, and insertion tube 160 is configured to create a more powerful fluid stream. As discovered and described in the present description, a more powerful fluid stream having a smaller fluid flow diameter is more effective at penetrating and breaking down ear wax lodged within the ear canal than existing, conventional devices which may only use one tube or tubes of similar sizes. Further, insertion tube 160 is configured to be shorter in length than conduit tube 130. In one exemplary embodiment, conduit tube 130 may be approximately 18 centimeters in length and insertion tube 160 may be approximately 3 centimeters in length.

Those of ordinary skill in the art appreciate that these measurements are non-limiting and other measurements may be used for conduit tube 130 and insertion tube 160.

Figure 5:
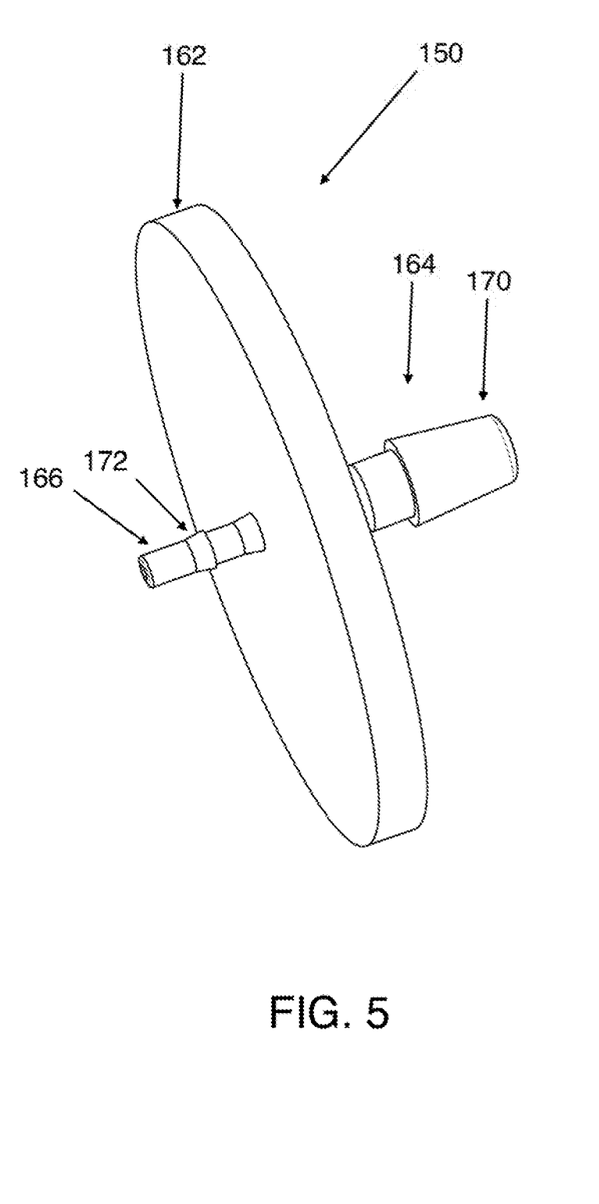
FIG. 5 illustrates a perspective view of a connector.

As illustrated in FIG. 5, connector 150 may have a splash guard portion such as splash guard portion 162, which prevents excess fluid or debris from splashing outward onto the user or the surrounding environment. In one embodiment, splash guard portion 162 is preferably transparent so as to allow the user or another or a third party observer to view the positioning of ear canal irrigation system 100 during use. Splash guard portion 162 is preferably circular and provided with an aperture generally located in the middle of the splash guard 162 to allow the passage of fluid. Further, splash guard portion 162 is configured to act as a lip that extends all the way around connector 150.

Additionally, in one embodiment, connector 150 has two extensions such as extensions 164 and 166 facing outward in opposite directions on each side of splash guard portion 162. Extensions 164 and 166 have apertures therethrough in axial alignment allowing the passage of fluid. Extensions 164 and 166 are designed so that both conduit tube 130 and insertion tube 160 may be connected without having to screw the tubes onto connector 150. Extensions 164 and 166 are each sized to fit, respectively, within conduit tube 130 and insertion tube 160. Specifically, extension 164 is configured so that the bottom end of conduit tube 130 may be slid over extension 164 until the conduit tube 130 comes into contact with one side of splash guard portion 162 in order to create an air tight seal. Similarly, extension 166 is configured so that the top end of insertion tube 160 may be slid over extension 166 until the insertion tube 160 comes into contact with the other side of splash guard portion 162 in order to create an air tight seal. Thus, the extensions 164 and 166 are sized and shaped to fit within conduit tube 130 and insertion tube 160, and to connect via connector 162. The selected shape and diameter of extensions 164 and 166 are designed to create an optimal flow of fluid with minimal resistance.

Extension 164, which is connectable to conduit tube 130 as shown in FIG. 5, may be formed having two parts whereby a bottom part is in the form of a shaft and a top part has a conical shape (e.g. 170) that that inclines at an angle. At the top end of extension 164, a bottom end of conduit tube 130 may be connected and secured by the conical shaped component such as conical shaped component 170 of extension 164, because conical shaped component 170 of extension 164 fits within conduit tube 130 when conduit tube 130 is slid or positioned over the outer area of conical shape component 170.

Extension 166 connected to insertion tube 160 may be formed having a circular shaft having one or more protrusions such as protrusions 172 that extend from the circular shaft. Extension 166 may also have a conical shape that also angles, whereby the insertion tube 160 may be connected and secured by the outward force of protrusions 172 against insertion tube 160 when the inner diameter of insertion tube 160 is slid or positioned over the outer area of protrusions 172 located on extension 166.

The following is a description of an exemplary method of using ear canal irrigation system 100 as shown in FIGS. 1-5. During operation or use, insertion tube 160 is oriented in or near the ear canal of a user. Trigger mechanism 114 may be pulled in a direction whereby the spray bottle tube 115 draws up any fluid located within reservoir 111. The fluid will then flow up spray bottle tube 115 out from reservoir 111 and into the internal chamber of head 112. Once fluid is present inside the internal chamber of head 112, fluid may be expelled out of nozzle 113 as trigger mechanism 114 is depressed. In one embodiment, the fluid from reservoir 111 may pass through nozzle attachment 120, into conduit tube 130, into connector 150 where the fluid enters and passes through insertion tube 160 and into the user's ear. The overall diameter of the fluid stream is optimally decreased when passing through connector 150 and into insertion tube 160 so as to create a more powerful fluid stream when the fluid goes from conduit tube 130 to insertion tube 160 and into the user's ear, which should optimally discharge a greater amount of ear wax than a fluid stream with a very wide fluid diameter. Additional fluid may be drawn up as needed by the user by continuously depressing and releasing trigger mechanism 114. User may pull trigger mechanism 114 in a direction and release as many times as needed or until fluid has been sufficiently depleted from reservoir 111 of spray bottle 110.

Prior to use, the following steps may be taken to connect the components together. Head 112 may be connected to reservoir 111 of spray bottle 110. Nozzle attachment 120 may be connected to nozzle 113. Conduit tube 130 may be connected to nozzle attachment 120. Cover piece 140 may be connected to nozzle attachment 120 thus creating a seal for fluids in conduit tube 130. Connector 150 may be connected to conduit tube 130 and insertion tube 160 may be connected to connector 150. It is also possible that a user may first connect nozzle attachment 120 to the cover piece 140, the conduit tube 130, the connector 150, and the insertion tube 160, such that all of these components are assembled as a unit, and then screw on or otherwise attach the bottom part (e.g. bottom component 122) of nozzle attachment 120 to nozzle 113. Advantageously, there are various ways to connect the pieces together to facilitate the assembly for the user.

There are several advantages offered by the one or more embodiments provided in the present description. The various components are customized to connect together and to also minimize leakage of fluid from the various parts. For example, bottom component 122 minimizes leakage of fluid coming from nozzle 113, and cover piece 140 acts as reinforcing seal when screwed on or otherwise attached to middle component 124 of nozzle attachment 120 to minimize or prevent leakage of fluid. Connector 150 may be beneficial and is unique for many reasons, including because in one or more embodiments, it may include a splash guard portion (e.g. splash guard portion 162) to minimize splashing of fluid on a user and the surrounding environment. Connector 150 may also be transparent so as to allow a user or third party to see clearly the placement of insertion tube 160 into a user's ear. Further, connector 150 allows the connection between conduit tube 130 and insertion tube 160 with a decrease in diameter of the tubing sizes between conduit tube 130 and insertion tube 160 which provides more power and greater fluid flow into a user's ear, which should dislodge a greater amount of ear wax from a user's ear. The spray bottle 110 and the various components included in the ear canal irrigation system 100 may be hand-held and easily portable, so that a user may use the system 100 anywhere he or she desires.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated. The present invention according to one or more embodiments described in the present description may be practiced with modification and alteration within the spirit and scope of the appended claims. Thus, the description is to be regarded as illustrative instead of restrictive of the present invention.

What is claimed is:

1. An ear canal irrigation system, the ear canal irrigation system comprising:
    a spray bottle, the spray bottle comprising a nozzle, a head, and a reservoir, the reservoir having a spray tube extending therethrough, wherein the reservoir is configured to contain a fluid;
    a conduit tube, wherein the conduit tube is configured to allow the passage of the fluid from the spray bottle when connected to the spray bottle, wherein a first end of the conduit tube is configured to connect to the nozzle or a nozzle attachment that is connected to the nozzle;
    a connector comprising a splash guard, a first extension piece, and a second extension piece, wherein the splash guard is disk-shaped, wherein the first extension piece and the second extension piece face outward in opposing directions from a first side and a second side of the splash guard, wherein the splash guard, the first extension piece, and the second extension piece each have an aperture therethrough in axial alignment allowing the passage of the fluid; and
    an insertion tube, wherein the insertion tube is configured to be inserted into or near an ear of a user, wherein the insertion tube is separate from the conduit tube,
    wherein a second end of the conduit tube is configured to connect to the first extension piece of the connector,
    wherein a first end of the insertion tube is configured to connect to the second extension piece of the connector,
    and further wherein the conduit tube and the insertion tube each have an aperture extending therethrough, wherein the aperture of the insertion tube is of a smaller diameter than the aperture of the conduit tube, wherein the connector allows a transition of the fluid from the conduit tube to the insertion tube while reducing the overall diameter of the fluid.

2. The ear canal irrigation system of claim 1, wherein the second end of the conduit tube is configured to be positioned over the first extension piece, and wherein the first end of the insertion tube is configured to be positioned over the second extension piece until the conduit tube and the insertion tube come into contact with the first side and the second side of the splash guard.

3. The ear canal irrigation system of claim 1, wherein the first extension piece includes a bottom part in the form of a shaft and a top part having a conical shape that inclines at an angle, wherein the first extension piece is configured to fit within the aperture of the conduit tube when connected, wherein the second extension piece is configured to fit within the aperture of the insertion tube when connected, wherein the second extension piece comprises a shaft having one or more protrusions from the shaft, wherein the insertion tube is configured to be connected and secured by the outward force of the one or more protrusions against the insertion tube when the inner diameter of the insertion tube is positioned over the outer area of the one or more protrusions.

4. The ear canal irrigation system of claim 1, wherein the second side of the splash guard is configured to impede a splash effect when fluid is expelled out of the insertion tube, wherein the splash guard is configured to shield the ear canal irrigation system and a user from splash back of the fluid.

5. The ear canal irrigation system of claim 1, wherein the insertion tube is shorter in length than the conduit tube.

6. The ear canal irrigation system of claim 1, where said conduit tube and insertion tube are comprised of a flexible material.

7. The ear canal irrigation system of claim 1, wherein the insertion tube is separately removeable from the conduit tube when connected to the connector.

8. The ear canal irrigation system of claim 1, wherein the first extension piece includes a bottom part in the form of a shaft and top part having a conical shape that inclines at an angle, wherein the first extension piece is configured to fit within the aperture of the conduit tube when connected.

9. The ear canal irrigation system of claim 1, wherein the second extension piece comprises a shaft having one or more protrusions from the shaft wherein the insertion tube is configured to be connected and secured by the outward force of the one or more protrusions against the insertion tube when the inner diameter of the insertion tube is slid or positioned over the outer area of the one or more protrusions.

10. The ear canal irrigation system of claim 1, wherein the nozzle attachment is configured to connect to a cover piece, the cover piece configured so that when connected to the nozzle attachment, the cover piece acts as a reinforcing seal to prevent any leakage of fluid as the fluid exits the nozzle into the conduit tube.

11. The ear canal irrigation system of claim 10, the cover piece having have a bottom and top component, the bottom and top component having apertures therethrough wherein the apertures in the bottom and top components of the cover piece are in axial alignment.

12. The ear canal irrigation system of claim 11, wherein the aperture of the top component of the cover piece has a diameter less than the diameter of the aperture of the bottom component of the cover piece, thereby allowing the cover piece to slide over the conduit tube until the bottom component of the cover piece comes in contact with the nozzle attachment.

13. A method of using an ear canal irrigation device, the method comprising:
    connecting a nozzle attachment to a nozzle of a spray bottle;
    connecting a conduit tube to the nozzle attachment;
    connecting the conduit tube to a first end of a connector, wherein the connector further comprises a splash guard, a first extension piece, and a second extension piece, wherein the splash guard is disk-shaped, wherein the first extension piece and the second extension piece face outward in opposing directions from a first side and a second side of the splash guard, wherein the splash guard, the first extension piece, and the second extension piece each have an aperture therethrough in axial alignment allowing the passage of the fluid;
    connecting an insertion tube to the second extension piece, wherein the conduit tube and the insertion tube have an aperture therethrough, wherein the aperture of the insertion tube is of a smaller diameter than the conduit tube, and wherein the connector allows for a transition of a fluid from the conduit tube to the insertion tube while reducing the overall diameter of the fluid; and orienting the insertion tube at or near the ear canal of a user.

14. The method of claim 13, the method further comprising: pulling a trigger mechanism of a spray bottle, the spray bottle comprising a reservoir to contain the fluid and a nozzle, wherein when the trigger mechanism is pulled, fluid flows from the reservoir and is then expelled out of the nozzle.

15. The method of claim 13, the method further comprising:

flowing the fluid from the nozzle to the conduit tube, the nozzle connecting to the nozzle attachment, the nozzle attachment connecting to the conduit tube, the nozzle attachment connecting to a cover piece, the cover piece when connected to the nozzle attachment acting as reinforcing seal to prevent any leakage of fluid as the fluid exits the nozzle into the conduit tube, the cover piece having a bottom and top component, the bottom and top component having apertures therethrough wherein the apertures in the bottom and top component of the cover piece are in axial alignment, the aperture of the top component having a diameter less than the diameter of the aperture of the bottom component, allowing the cover piece to slide over the conduit tube until the bottom component of the cover piece comes in contact with the nozzle attachment.

16. An ear canal irrigation system, the ear canal irrigation system comprising:

a spray bottle, the spray bottle comprising a nozzle, a head, and a reservoir, the reservoir having a spray tube extending therethrough, wherein the reservoir is configured to contain a fluid;

a nozzle attachment, wherein the nozzle attachment is configured to connect to the nozzle;

a conduit tube, wherein the conduit tube is configured to connect to the nozzle attachment at a first end of the conduit tube;

a connector comprising a splash guard, and a first extension piece, and a second extension piece, wherein the splash guard is disk-shaped, wherein the first extension piece and the second extension piece face outward in opposing directions from a first side and a second side of the splash guard, wherein the splash guard, the first extension piece, and the second extension piece each have an aperture therethrough in axial alignment allowing the passage of the fluid; and an insertion tube, wherein the conduit tube is configured to connect to the first extension piece at a second end of the conduit tube, and wherein the insertion tube is configured to connect to the second extension piece at a first end of the insertion tube, and further wherein the conduit tube and the insertion tube each have an aperture extending therethrough, wherein the aperture of the insertion tube is of a smaller diameter than the aperture of the conduit tube, wherein the connector allows a transition of the fluid from the conduit tube to the insertion tube while reducing the overall diameter of the fluid.

17. The ear canal irrigation system of claim 16, a cover piece, wherein the nozzle attachment is configured to connect to the cover piece, the cover piece configured so that when connected to the nozzle attachment, the cover piece acts as a reinforcing seal to prevent any leakage of fluid as the fluid exits the nozzle into the conduit tube.

18. The ear canal irrigation system of claim 16, wherein the first extension piece and the second extension piece are configured such that the second end of the conduit tube and a first end of the insertion tube are configured be slid over the first extension piece and the second extension piece, respectively, until the conduit tube and insertion tube come into contact with opposite surfaces of the splash guard.

19. The ear canal irrigation system of claim 16, wherein the first extension piece includes a bottom part in the form of a shaft and top part having a conical shape that inclines at an angle, wherein the first extension piece is configured to fit within the aperture of the conduit tube when connected, wherein the second extension piece comprises a shaft having one or more protrusions from the shaft wherein the insertion tube is configured to be connected and secured by the outward force of the one or more protrusions against the insertion tube when the inner diameter of the insertion tube is slid or positioned over the outer area of the one or more protrusions.

* * * * *